United States Patent [19]

Anatol et al.

[11] 4,013,706

[45] Mar. 22, 1977

[54] DERIVATIVES OF SUBSTITUTED UREA, ACYL UREAS, AND SULPHONYL UREAS, AND A PROCESS FOR PRODUCING THE SAME

[75] Inventors: Jesus Anatol, Paris; Jean Berecoechea, Reims, both of France

[73] Assignee: Sucreries du Soissonnais et Compagnie Sucriere, Paris, France

[22] Filed: Nov. 13, 1974

[21] Appl. No.: 523,550

[30] Foreign Application Priority Data

Nov. 14, 1973  France .................... 73.40527
Oct. 25, 1974  France .................... 74.35907

[52] U.S. Cl. .......... 260/471 C; 260/456 A; 260/468 E; 260/479 C; 260/482 C; 260/551 C; 260/553 R; 260/553 A; 260/553 D; 260/553 E; 260/556 R; 260/556 A; 260/556 AR; 260/557 R; 260/558 R; 260/561 R; 260/562 R

[51] Int. Cl.² ...................... C07C 125/06
[58] Field of Search ....... 260/471 C, 456 A, 553 R, 260/553 A, 553 D, 553 E, 482 C, 468 E, 479 C

[56] References Cited

UNITED STATES PATENTS

| | | | |
|---|---|---|---|
| 3,332,994 | 7/1967 | Marsh | 260/553 R X |
| 3,427,323 | 2/1969 | Marsh | 260/553 R X |
| 3,748,356 | 7/1973 | Wellinga et al. | 260/553 E |

OTHER PUBLICATIONS

Karrer, Organic Chemistry, Elsevier Publishing Company, Inc., New York (1950) pp. 231 to 233.

*Primary Examiner*—Richard L. Raymond
*Attorney, Agent, or Firm*—Karl W. Flocks

[57] ABSTRACT

A process for the production of compounds of the general formula:

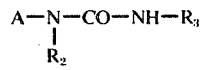

and compounds of that general formula, in which A represents hydrogen or an $R_1 - X$ group (in which X represents $-CO$ or $-SO_2$ and $R_1$ represents an optionally substituted alkyl, cycloalkyl, aralkyl, alkoxy, aryl, aryloxy, etheroxy, aliphatic or aromatic group), $R_2$ represents a hydrogen atom or an optionally substituted alkyl, cycloalkyl, aralkyl, or aryl group, and $R_3$ represents a hydrogen atom or an alkyl group derived from a secondary or tertiary alcohol, particularly a tertio-butyl group, with the restriction that, when $R_2$ represents hydrogen, $R_3$ represents the said alkyl group and that, when $R_3$ represents hydrogen, $R_2$ represents the said optionally substituted alkyl, cycloalkyl, aralkyl, or aryl group, the said process comprising reacting a cyanamide of the formula:

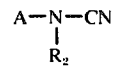

(in which A and $R_2$ have the meanings given above) with a compound e.g. a tertiary or secondary alcohol adapted to form readily a carbo cation ($R_3^+$) in the presence of a catalyst e.g. sulphuric acid or a Lewis acid.

5 Claims, No Drawings

DERIVATIVES OF SUBSTITUTED UREA, ACYL UREAS, AND SULPHONYL UREAS, AND A PROCESS FOR PRODUCING THE SAME

BACKGROUND OF THE INVENTION

1. Field of the Invention

The present invention relates to ureas, acylureas, and sulphonylureas corresponding to the general formula:

in which A represents hydrogen or an $R_1 - X$ group (in which X represents $-CO$ or $-SO_2$ and $R_1$ represents an optionally substituted alkyl, cycloalkyl, aralkyl, alkoxy, aryl, aryloxy, etheroxy, aliphatic or aromatic group), $R_2$ represents a hydrogen atom or an optionally substituted alkyl, cycloalkyl, aralkyl, or aryl group, and $R_3$ represents a hydrogen atom or an alkyl group, particularly a tertiobutyl group.

The invention has as objects a process for the production of these compounds and also the new compounds which can be obtained with the aid of this process.

2. Description of the Prior Art

Various compounds are in fact known which correspond to the general formula (I) above, in which the symbols A, $R_2$, and $R_3$ have the meanings given, but which are not substituted in position 3 ($R_3$ representing a hydrogen atom) or are monosubstituted in that position ($R_3$ not representing hydrogen) or are disubstituted in that position ($NH-R_3$ representing an

group with $R_3$ not representing hydrogen), and/or which, in position 1, are not substituted (A and $R_2$ each representing hydrogen) or are monosubstituted (one of the two symbols A or $R_2$ representing hydrogen).

However, no compounds disubstituted in position 1 and monosubstituted in position 3 are known. The process of the invention, as it will be defined hereinbelow, makes it possible not only to obtain in a general way the compounds of formula (I) above, but also to isolate the new compounds.

Various more or less effective processes have in fact been proposed for obtaining compounds of the formula:

in which $R_1 - X$ and $R_3$ have the meanings given above for formula (I).

The processes most frequently used are the following:

1. Action of an isocyanate on a sulphonamide or an amide in a generally alkaline medium:

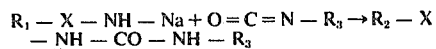

2. Action of an acyl or sulphonyl isocyanate on an amine:

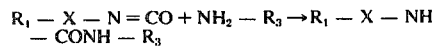

3. Action of an aliphatic chlorocarbonate on a sulphonamide:

a) 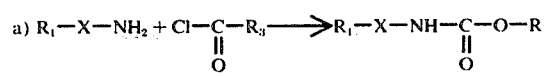

b. Action of acyl or sulphonyl urethane thus obtained on an amine at high temperature:

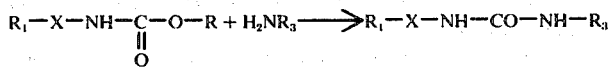

These processes often give rise to a certain number of difficulties and do not always make it possible to obtain the expected result with a good yield.

SUMMARY

The present invention reduces or obviates these disadvantages and has as its object a simple, economical, and profitable general process for producing ureas of formula (I) above, which process consists in reacting a cyanamide of the formula:

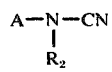

(in which A and $R_2$ have the meanings given above for formula (I) with a compound adapted to form readily a carbo cation $R_3^+$ in the presence of a catalyst.

The compound adapted to form readily a carbo cation $R_3^+$ may be selected from the following: tertiary alcohols, secondary alcohols, unsaturated compounds.

The catalyst may be sulphuric acid or a Lewis acid in the presence or absence of a solvent for the starting cyanamide.

As the result of the process of the invention, the Applicants have been able to isolate new acyl or sulphonyl-1 urea compounds substituted in positions 1 and 3, of formula (I).

Other characteristics and advantages of the invention will be seen more clearly from the description given below.

It is known that by extension of Ritter's reaction it is possible to convert fragile α-substituted nitriles (α-amino nitriles, cyanhydrines) into α-substituted N-tertiobutyl amides in accordance with the reactional structural formula:

obutyl-3 urea by the action of phenyl isocyanate on tertiobutylamine in accordance with the equation:

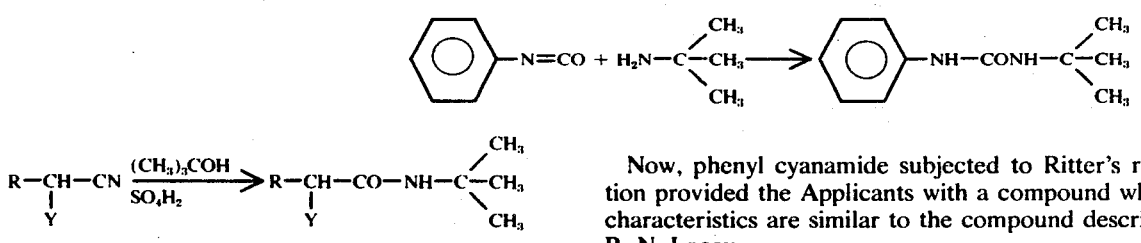

Now, phenyl cyanamide subjected to Ritter's reaction provided the Applicants with a compound whose characteristics are similar to the compound described R. N. Lacey.

(in which for the sake of simplification R and Y represent suitable substituents).

After experimentation the Applicants have now unexpectedly found that cyanamides of the formula:

 (IV)

or the same acylated or sulphonylated cyanamides of the formula:

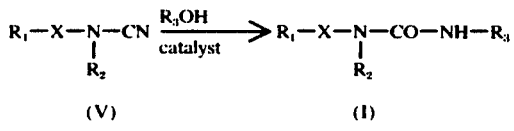 (V)

are also able, through their nitrile function, to react positively to the conditions of Ritter's reaction and to lead unequivocally to the ureas and acyl or sulphonyl ureas of the general formula (I), particularly to ureas and acyl or sulphonyl ureas substituted in position 1 and 3, in accordance with the equation:

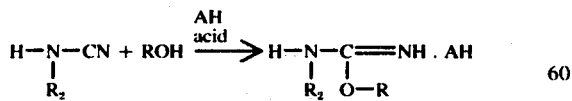

(V)          (I)

This is all the more surprising and remarkable because it is generally accepted that the action of an alcohol on cyanamides in the presence of acids (AH) leads to isourea salts in accordance with the equation:

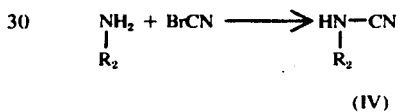

Moreover, the Applicants assured themselves that the compounds obtained from the Ritter's reaction on the cyanamides definitely had the urea structure of formula (I) by comparison with known products prepared by conventional methods. Thus, for example, R. N. Lacey (Soc. 1960, 1633) prepared phenyl-1-tertiobutyl-3 urea by the action of phenyl isocyanate on tertiobutylamine in accordance with the equation:

Spectroscopic measurements (IR and NMR) moreover confirm the urea constitution of this compound.

The cyanamides serving as intermediate products according to the invention are prepared in a simple manner by the action of the cyanogen bromide produced "in situ" ($Br_2 + CNK + H_2O \rightarrow BrCN + BrK$) on the amines in accordance with the equation:

$$NH_2 + BrCN \longrightarrow HN-CN$$
$$| \qquad\qquad\qquad |$$
$$R_2 \qquad\qquad\qquad R_2$$

(IV)

By the well known method of Scotte Baumann these cyanamides are converted without any difficulty into acyl or sulphonyl cyanamides in accordance with the equation:

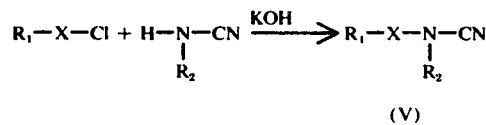

(V)

of which few representatives are known at the present time.

Thus, these cyanamides — either free (formula IV) or acylated or sulphonylated (formula V) - — subjected to the conditions of Ritter's reaction in accordance with the invention make it possible to obtain, with very good yields, differently substituted ureas which for the most part are new and whose structure is that indicated by the general formula (I).

The well known hydration of these acylated or sulphonylated cyanamides produces, with excellent results, new acyl or sulphonyl-1 ureas substituted at 1 ($R_3$ = H) in accordance with the equation:

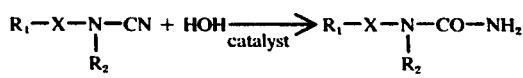

DETAILED DESCRIPTION OF THE INVENTION

The following examples are given by way of illustration and without limitation in any way.

In these examples, compounds accompanied by an asterisk (*) are known compounds.

EXAMPLE 1.

Dimethyl 2,3 phenyl cyanamide 27.3 ml (0.5 M) of bromine in 160 ml of water are poured into a three-necked flask. 34.6 g (0.5 M) of potassium cyanide dissolved in 320 ml of water are added, with mechanical agitation, with the aid of a bromine funnel, and while cooling so that the temperature remains below 10° C.

The reaction medium loses colour at the end of the addition. While maintaining the agitation and the above-mentioned temperature, 121 g (1M) of dimethyl-2,3-aniline are then added with the aid of a bromine ampoule.

At the end of 3 hours the oily droplets are solidified. The product is filtered, washed with water on the filter, and then dried and recrystallised from benzene. 66 g of product melting at 124° C are obtained; yield = 90%.

| Analysis: | $C_9H_{10}N_2$; M = 146 | | |
|---|---|---|---|
| | C | H | N |
| Calculated: | 73.94 | 6.89 | 19.16 |
| Found: | 73.99 | 7.05 | 19.20 |

EXAMPLE 2

Phenyl cyanamide (*)

The procedure is as in Example 1, by substituting aniline for dimethyl-2,3-aniline. After filtration, the mixture is washed with water on the filter and the crude product is used. Yield is quantitative. The product eventually polymerises.

EXAMPLE 3

Meta-tolyl cyanamide (*)

The procedure is the same as previously, applied to meta-toluidine. The yield is quantative. The product eventually polymerises.

EXAMPLE 4

Tertio-butyl cyanamide (*)

The same procedure as previously, applied to tertio-butylamine. As the resulting product is liquid, it is extracted with ether, washed with water, dried, the ether is evaporated under reduced pressure, and the product distilled. B.P. 115°/15 mm. Yield = 68%.

EXAMPLE 5

Production of N,N'-di-tert.butyl urea

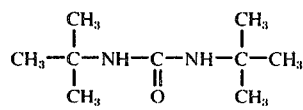

This product is well known and has often been described in chemical literature (see for example "Org. Synthesis Coll.", Volume III, 155 (1955); C.A. 35, 6267 (1941); C.A. 45 8037$^b$; 52, 10164$^n$; C.A. 53, 5297$^a$).

To the extent to which this product is of commercial interest, it can be obtained easily and economically by the process of the invention, in which the operating procedure may be as follows:

With magnetic agitation, 4.90 g (50 mM) of tertiobutyl cyanamide are added to 20 ml (4 vol) of tertiobutanol, and then 12.5 ml of boron fluoroetherate. The solution is left for one hour with agitation at ambient temperature, and then poured on to 100g of a mixture of water and ice. A precipitate is formed, which is filtered and washed with water.

In order to purify it, the product obtained is heated in 40 ml of boiling water, whereupon it is drained and rinsed with 15 ml of boiling water.

After drying there are obtained 4.19 g (yield 48.7%) of N,N'-di-tert.butyl urea, with a melting point of 246° C (in sealed capillary) (literature: 243° C).

Analysis: $C_9H_{20}N_2O$; M = 172. Nitrogen: Calculated: 16.25%. Found: 16.36%.

EXAMPLE 6

Dimethyl-2,3-phenyl-tosyl cyanamide 5.84 g (40 mM) of dimethyl-2,3-phenyl cyanamide are dissolved in 20 ml of 2.5 N potassium hydroxide, with magnetic agitation, 8.38 g (44 mM) of tosyl chloride dissolved in 20 ml of acetone are added, while cooling. Agitation is maintained for 3 hours. The acetone is evaporated under reduced pressure. The product is recrystallized from ethanol. 10 g of product are obtained. Yield = 83%. MP = 110° C.

| Analysis: | $C_{16}H_{16}N_2O_2S$; M = 300 | | |
|---|---|---|---|
| | C | H | N |
| Calculated: | 64.00 | 5.33 | 9.33 |
| Found: | 63.91 | 5.28 | 9.40 |

The following Table illustrates certain other examples of intermediate cyanamide compounds which can be obtained, corresponding to the formula:

$$R_1-X-N(R_2)-C\equiv N$$

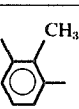

| Example | $R_1-X-$ | $R_2$ | Fusion ° C | Recrystallisation solvents |
|---|---|---|---|---|
| 7 | $CH_3-C_6H_4-SO_2-$ | 2,6-dimethylphenyl | 110° | Ethanol |

-continued $$R_1-X-N(R_2)-C\equiv N$$

| Example | $R_1-X-$ | $R_2$ | Fusion °C | Recrystallisation solvents |
|---|---|---|---|---|
| 8 | $NO_2$-C₆H₄-$SO_2-$ (4-NO₂) | 2,3-dimethylphenyl | 165° | Acetone-water |
| 9 | C₆H₄(2-$NO_2$)-$SO_2-$ | 2,3-dimethylphenyl | 155° | Acetone-water |
| 10 | $NO_2$-C₆H₄-$SO_2-$ (4-NO₂) | 3-methylphenyl | 150° | Acetone-water |
| 11 | C₆H₄(2-$NO_2$)-$SO_2-$ | 3-methylphenyl | 112° | Acetone-water |
| 12 (*) | $CH_3$-C₆H₄-$SO_2-$ | phenyl | 76° | Ethanol-water |
| 13 | C₆H₄(2-$NO_2$)-$SO_2-$ | phenyl | 145° | Ethyl acetate |
| 14 | C₆H₅-CO- | phenyl | 118° | Ethyl acetate |
| 15 | C₆H₅-CO- | 3-methylphenyl | 65° | Ethanol |
| 16 | $CH_3-SO_2-$ | 2,3-dimethylphenyl | 98° | Ethanol |
| 17 | $CH_3-SO_2-$ | phenyl | Oil | Utilised crude |
| 18 | Cl-C₆H₄-O-$CH_2$-CO- | 2,3-dimethylphenyl | 155° | Ethyl acetate |
| 19 | Cl-C₆H₄-O-$CH_2$-CO- | phenyl | 148° | Benzene-ethanol or acetone |
| 20 | $C_2H_5$-O-CO- | 2,3-dimethylphenyl | 57° | Ethanol-water |
| 21 (*) | $C_2H_5$-O-CO- | phenyl | Oil | Utilised crude |
| 22 | C₆H₅-CO- | 2,3-dimethylphenyl | 85° | Ethyl acetate Petroleum ether |

-continued

| | | | | Recrystallis- |
|---|---|---|---|---|
| Example | R₁—X— | R₂ | Fusion °C | ation solvents |
| 23 | 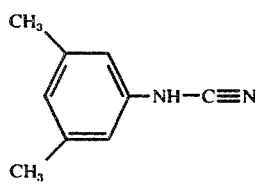 | 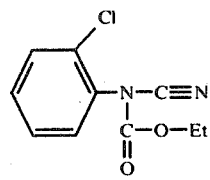 | 118° | Ethanol |

EXAMPLE 24

Dimethyl-3,5-phenyl cyanamide (compound No. 98)

$$\text{CH}_3\text{-C}_6\text{H}_3(\text{CH}_3)\text{-NH-C}\equiv\text{N}$$

150 ml of water and 26 ml of bromine (0.5 mole) are introduced, in accordance with the process described in Example 1, into a 1-litre three-necked flask provided with an efficient agitation system, an introduction funnel, and a thermometer, and cooled to 10°–15° C by a bath of water and ice. With the aid of the introduction funnel there are added, within a period of about 30 minutes and while making sure that the temperature of the mixture does not exceed 15° C, a solution of 33 g (0.5 mole) of potassium cyanide. At the end of this addition, the mixture loses its colour.

While the temperature is thereupon kept at about 15° C with the aid of the ice bath, 121 g (1 mole) of dimethyl-3,5-aniline (over a period of 30 minutes) are added, and the mixture is then allowed to return to ambient temperature, while agitation is continued for three hours.

The precipitate obtained is then drained and abundantly washed with water to entrain the dimethyl-3,5-aniline hydrobromide, which is sparingly soluble. After drying in a desiccator under vacuum, there are obtained 69.2 g of product, which is recrystallised from 2.5 volumes of benzene in the presence of carbon black.

After drying there are obtained: 62.4 g of dimethyl-3,5-phenyl cyanamide.

MP = 124°–125° C (Kofler bench)
Yield = 85.5%

This new compound makes it possible to obtain, in accordance with the reaction:

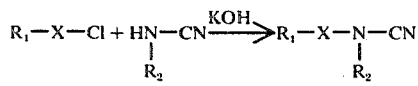

the following new products:

(Dimethyl-3,5-phenyl) carbethoxy cyanamide (compound No. 101) by reaction with ethyl chloroformate (ClCOOEt); (dimethyl-3,5-phenyl) (chloro-4-phenoxyacetyl)cyanamide (compound No. 104) by reaction with the chloride of chloro-4-phenoxyacetic acid; (dimethyl-3,5-phenyl) (trichlor-2,4,5-phenoxyacetyl)-cyanamide (compound No. 102) by reaction with the chloride of trichloro-2,4,5-phenoxyacetic acid; and (dimethyl-3,5-phenyl) (trimethoxy-3,4,5-benzoyl) cyanamide (compound No. 105) by reaction with the chloride of trimethoxy-3,4,5-benzoic acid.

EXAMPLE 25

(Chloro-2-phenyl)carbethoxy cyanamide (compound No. 99)

$$\text{2-Cl-C}_6\text{H}_4\text{-N(C}\equiv\text{N)-C(=O)-O-Et}$$

13.72 g (0.09 mole) of chloro-2-phenyl cyanamide (a known product) and a solution of 6.5 g of potassium hydroxide in pastilles (0.099 mole) in 50 ml of water are introduced into a 100-ml three-necked flask provided with an agitation system, a thermometer, and an introduction funnel protected against moisture by a trap filled with calcium chloride. A clear solution is obtained, which is cooled with a bath of water and ice. With good agitation and without allowing the temperature of the mixture to rise above 15° C, there are added drop by drop through the introduction funnel: 9.4 ml (0.099 mole) of ethyl chloroformate

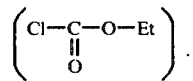

This addition is effected within 10 minutes. The mixture is then allowed to return to ambient temperature, and agitation is continued for 1 hour.

An oil is formed. It is extracted several times with ether, the ether phase is washed with water to neutrality, and then it is dried over anhydrous sodium sulphate.

After the ether has been driven off, the product is distilled in vacuo. There are obtained 17.35 g of a colourless liquid compound:

$E_{0.15}$ = 134°–137° C.

Yield = 86%, corresponding to the above formula.

By proceeding in the same manner with chloro-2 phenylcyanamide it is possible to obtain the following new compounds:

(chloro-2 phenyl)(chloro-4 phenoxyacetyl)cynamide (compound No. 87) by reaction with the chloride of chloro-4 phenoxyacetic acid, and (chloro-2)(dichloro-2,4 phenoxyacetyl)cyanamide (compound No. 88) by reaction with the chloride of dichloro-2,4 phenoxyacetic acid.

Similarly, by reacting chloro-3 phenylcyanamide with ethyl chloroformate, the chloride of chloro-4 phenoxyacetic acid, or the chloride of dichloro-2,4 phenxoyacetic acid, there are obtained respectively (chloro-3 phenyl) carbethoxy cyanamide (compound No. 111), (chloro-3 phenyl) (chloro-4 phenoxyacetyl) cyanamide (compound No. 89), and (chloro-3 phenyl)(dichloro-2,4 phenoxyacetyl) cyanamide (compound No. 90), which are new compounds.

Furthermore, by reacting chloro-4 phenylcyanamide with the chloride of chloro-4 phenoxyacetic acid or with the chloride of dichloro-2,4 phenoxyacetic acid, there are obtained respectively the following new compounds: (chloro-4 phenyl)(chloro-4 phenoxyacetyl) cyanamide (compound No. 91) and (chloro-4 phenyl)-(dichloro-2,4 phenoxyacetyl) cyanamide (compound No. 92).

Moreover, by reacting dichloro-3,4 phenylcyanamide with ethyl chloroformate, the chloride of chloro-4 phenoxyacetic acid, or the chloride of dichloro-2,4 phenoxyacetic acid, there are obtained respectively the following new cyanamides:

(dichloro-3,4 phenyl) carbethoxycyanamide (compound No. 94),
(dichloro-3,4 phenyl)(chloro-4 phenoxyacetyl) cyanamide (compound No. 83), and
(dichloro-3,4 phenyl)(dichloro-2,4 phenoxyacetyl) cyanamide (compound No. 84).

EXAMPLE 26

(Methyl-4 phenyl)(nitro-2 phenylsulphonyl)cyanamide (compound No. 69).

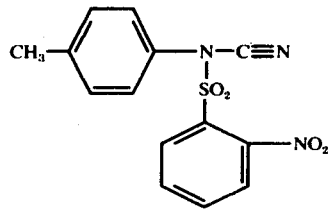

In accordance with the process described in Example 6 there are introduced into a 500-ml flask provided with an agitation device, a thermometer, and an introduction funnel: 26.4 g (0.2 mole) of methyl-4 phenyl cyanamide (known product) and a solution of 14.5 g (0.22 mole) of potassium hydroxide in pastilles in 100 ml of water. The mixture is cooled with a bath of water and ice to +10° C and, while making sure that the temperature of the mixture is kept between 10° and 15° C., there are added: 48 g (0.22 mole) of nitro-2 phenylsulphonyl chloride dissolved in 100 ml of acetone.

Precipitation is immediate. The addition takes 30 minutes. The product is then allowed to return to ambient temperature and agitation is continued for 4 hours.

The precipitate is then filtered and washed with water on the filter to neutrality. After drying in a dessicator, the resulting solid is recrystallised from 5 volumes of an 80:20 mixture of ethanol and isopropyl ether. After drying there are obtained 46.18 g of (methyl-4 phenyl)(nitro-2 phenyl sulphonyl) cyanamide, M.P. 120° C. (Kofler bench); yield = 73%. This product is a new cyanamide, which is also true of methyl-4 phenyl carbethoxy cyanamide (compound No. 95) obtained by reacting methyl-4 phenyl cyanamide with ethyl chloroformate, and of (methyl-4 phenyl)(trimethoxy-3,4,5 benzoyl)cyanamide (compound No. 41) obtained by reacting methyl-4 phenyl cyanamide with the chloride of trimethoxy-3,4,5 benzoic acid.

By proceeding in the same manner, but starting with dimethyl-2,3 phenyl cyanamide (a new product obtained in accordance with Example 1) there are obtained:

by reacting with nitro-3 phenylsulphonyl chloride the new product (dimethyl-2,3 phenyl)(nitro-3 phenylsulphonyl)cyanamide (compound No. 59); by reacting with the chloride of dichloro-2,4 phenoxyacetic acid the new product (dimethyl-2,3 phenyl)(dichloro-2,4 phenoxyacetyl)cyanamide (compound No. 86); by reacting with the chloride of chloro-4 methyl-2 phenoxyacetic acid the new product (dimethyl-2,3 phenyl)(chloro-4 methyl-2 phenoxyacetyl) cyanamide (compound No. 106); by reacting with the chloride of trichloro-2,4,5 phenoxyacetic acid the new product (dimethyl-2,3 phenyl)(trichloro-2,4,5 phenoxyacetyl) cyanamide (compound No. 107); by reacting with chloroacetic acid the new product (dimethyl-2,3 phenyl) chloracetylcyanamide (compound No. 108). Starting with phenylcyanamide there is also obtained the new product phenyl-1(nitro-3 phenylsulphonyl) cyanamide (compound No. 57).

EXAMPLE 27.

Benzoyl-1 phenyl-1 tertiobutyl-3 urea

With magnetic agitation, 2.22 g (10 mM) of benzoyl phenylcyanamide are added to 9 ml (4 vol) of tertiobutanol, followed by 10 ml of acetic acid in order to assist solubilisation, and finally 1.1 ml (20 mM) of concentrated sulphuric acid added drop by drop while preventing the temperature from exceeding 40° C. The mixture is then heated for 1 hour at 50° C (temperature of the bath). It is allowed to stand for 16 hours. 50 ml of water are added, and the mixture is neutralised with concentrated caustic soda in the presence of phenolphthalein. The solid formed is filtered. It is recrystallised from a mixture of ethanol and water. A product melting at 102° C is obtained. Yield = 85%.

| Analysis: | $C_{18}H_{20}N_2O_2$; M = 296 | | |
|---|---|---|---|
| | C | H | N |
| Calculated: | 72.95 | 6.80 | 9.45 |
| Found: | 72.98 | 6.61 | 9.56 |

EXAMPLE 28

(Dimethyl-2,3 phenyl)-1 tosyl-1 tertiobutyl-3 urea

With magnetic agitation there are added 3 g (10 mM) of dimethyl-2,3 phenyl tosylcyanamide to 12 ml (4 vol.) of tertiobutanol, followed by 6 ml of boron fluoroetherate. In order to complete dissolution, 5 ml of dioxane are added. The mixture is allowed to stand for 16 hours. It is then heated for 1 hour at 75° C. After cooling, 50 ml of water are added. Setting is initiated. The product is filtered and recrystallised from a mixture of ethanol and water or from ethyl acetate. Yield = 60%. MP = 110° C.

Analysis: $C_{10}H_{14}N_2O_3S$; M = 242

|  | C | H | N |
|---|---|---|---|
| Calculated: | 49.58 | 5.78 | 11.57 |
| Found: | 49.40 | 5.87 | 11.61 |

The following Table illustrates the above products, and also other products according to the invention which correspond to the formula:

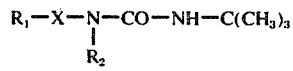

acid are heated with reflux for 30 minutes. After cooling, setting is observed. The product is filtered and recrystallised from a mixture of ethanol and isopropyl oxide.

MP = 158° C.
Yield = 60%.

Analysis: $C_{10}H_{14}N_2O_3S$ M = 242

|  | C | H | N |
|---|---|---|---|
| Calculated: | 49.58 | 5.78 | 11.57 |
| Found: | 49.40 | 5.87 | 11.61 |

| Example | $R_1-X-$ | $R_2$ | Fusion °C | Process | Recrystallisation solvent | Yields |
|---|---|---|---|---|---|---|
| 27 | phenyl-CO- | phenyl- | 105° C | Example 27 | Ethanol | 85 % |
| 28 | $CH_3$-phenyl-$SO_2$- | 2,3-dimethylphenyl- | 110° | Example 28 | Ethyl acetate or ethanol-water | 60 % |
| 29 | $NO_2$-phenyl-$SO_2$- | 2,3-dimethylphenyl- | 155° | Example 28 | Acetone-water | 70 % |
| 30 | 2-$NO_2$-phenyl-$SO_2$- | 2,3-dimethylphenyl- | 135° | Example 28 | Acetone-water | 74 % |
| 31 | $NO_2$-phenyl-$SO_2$- | 3-methylphenyl- | 140° | Example 28 | Ethanol or acetone-water | 75 % |
| 32 | 2-$NO_2$-phenyl-$SO_2$- | 3-methylphenyl- | 111° | Example 28 | Ethanol | 60 % (losses) |
| 33 | $CH_3$-phenyl-$SO_2$- | phenyl- | 110° | Example 28 | Isooxide or ethanol | 60 % |
| 34 | 2-$NO_2$-phenyl-$SO_2$- | phenyl- | 165° | Example 28 | Acetone-water or ethyl acetate | 74 % |
| 35 | phenyl-CO- | H | 142° | Example 27 | Ethanol-water | 70 % |
| 36 (*) | H | phenyl- | 169° | Example 27 | Ethanol or ethyl acetate | 62 % (losses) |

EXAMPLE 37

(dimethyl-2,3 phenyl)-1 mesyl-1 urea 4 g of (dimethyl-2,3 phenyl) mesyl cyanamide in 10 ml of ethanol and 5 ml of concentrated hydrochloric The following Table illustrates this product and also other products according to the invention which correspond to the formula:

| Example | R₁—X | R₂ | Fusion | Recrystallisation solvent | Yield |
|---|---|---|---|---|---|
| 37 | CH₃—SO₂— | 2,6-dimethylphenyl | 158° | Ethanol-iso-oxide | 60 % |
| 38 | C₂H₅—O—CO— | 2,6-dimethylphenyl | 180° | Ethanol-water | 80 % |
| 39 | CH₃—SO₂— | phenyl | 175° | Ethanol | 60 % |
| 40 | C₂H₅—O—CO— | phenyl | 150° | Ethyl acetate or ethanol | 90 % |

Structure heading: R₁—X—N(R₂)—CO—NH₂

EXAMPLE 41

(Methyl-4 phenyl)-1(nitro-2 phenylsulphonyl)-1 tertiobutyl-3 urea (compound No. 53)

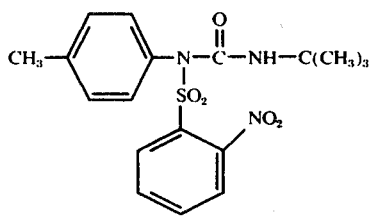

27.5 g (0.867 mole) of (methyl-4 phenyl)(nitro-2 phenylsulphonyl)cyanamide (obtained as described in Example 26, compound No. 69), 104 ml of dioxane, and 104 ml of tertiobutanol are introduced into a 500 ml three-necked flask provided with a magnetic agitation device, a cooler, and an introduction funnel, these devices being protected against moisture by traps filled with calcium chloride. 52 ml of boron trifluoride etherate are added fairly quickly through the introduction funnel, and then the mixture is progressively heated on an oil bath to 60° C, this temperature then being maintained for two hours. The resulting oily mixture is poured direct onto one liter of cold water, with agitation. A precipitate is formed, which is filtered and then washed with water to neutrality.

After drying in a desiccator in vacuo, the product is recrystallized from 4 volumes of ethanol in the presence of carbon black. 28.3 g of the above new urea are obtained in the form of white crystals. MP = 130° C (Köfler bench); yield = 83.5%.

In the same manner the following new ureas are obtained:

(methyl-4 phenyl)-1 benzoyl-1 tertiobutyl-3 urea (compound No. 40) from methyl-4 phenyl-1 benzoyl cyanamide;

(trimethoxy-3,4,5 benzoyl)-1 tertiobutyl-3 urea (compound No. 51) from trimethoxy-3,4,5 benzoyl cyanamide, and phenyl-1(nitro-3 phenylsulphonyl)-1 tertiobutyl-3 urea (compound No. 56) from phenyl-1 (nitro-3 phenylsulphonyl) cyanamide (compound No. 57).

EXAMPLE 42

(Chloro-2 phenyl)-1 carbethoxy-1 urea (compound No. 100) from (chloro-2 phenyl) carbethoxy cyanamide (compound No. 99)

10 g (0.0445 mole) of (chloro-2 phenyl)carbethoxycyanamide (compound No. 99), 20 ml of absolute alcohol, and 10 ml of concentrated hydrochloric acid ($d = 1.19$) are heated with reflux for one hour by the process described in Example 37 in a 50-ml flask fitted with a cooler. After draining and drying, the product is recrystallised from 3 volumes of ethanol, and there are obtained 9.36 g (yield = 86%) of the new urea of the formula given below, the product being in the form of elegant white needles melting at 152° C (Köfler bench):

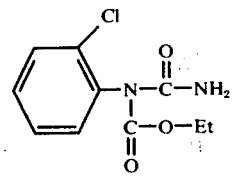

In the same way the new product (methyl-4 phenyl)-1 carbethoxy-1 urea (compound No. 97) is obtained from methyl-4 phenyl carbethoxy cyanamide (compound No. 95), and the new product (chloro-3 phenyl)-1 carbethoxy-1 urea from chloro-3 phenyl)carbethoxy cyanamide (compound No. 111).

The following table summarises the new compounds obtained according to the invention, giving their formulae and certain analysis results.

TABLE

A) Formula: R₂—NH—C≡N

| Compound No. | R₂ | Recrystallisation | M.P. °C | Yield % |
|---|---|---|---|---|
| 98 | 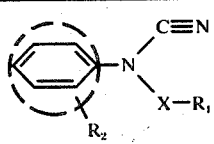 | Benzene, 2.5 vol. | 124–5 | 85.5 |

| | Analysis | | | |
|---|---|---|---|---|
| | C % | H % | N % | Remarks |
| | | | | New |

B) Formula:

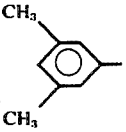

| Compound No. | X—R₁ | Recrystallisation | M.P. °C | Yield % |
|---|---|---|---|---|
| 57 | NO₂ / SO₂ (cyclohexane) | ACOEt : 2 vol. | 115 | 72 % |

| | Analysis | | | |
|---|---|---|---|---|
| | C % | H % | N % | Remarks |
| | | | | New |

C) Formula:

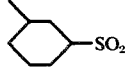

| Compound No. | X—R₁ | Recrystallisation | M.P. °C | Yield % |
|---|---|---|---|---|
| 95 | Eto—CO | MeOH . H₂O (2:1) 10 volumes | 50.1 | 73.5 |
| 41 | 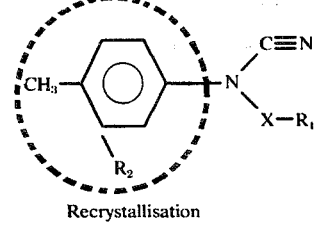 | C₂H₅OH 5 volumes | 121 | 72.5 |

| | Analysis | | | |
|---|---|---|---|---|
| | C % | H % | N % | Remarks |
| Calc. | 66.25 | 5.56 | 8.58 | New |
| Found | 65.96 | 5.50 | 8.65 | New |

D) Formula:

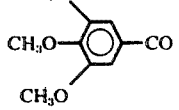

| Compound No. | X—R₁ | Recrystallisation | M.P. °C | Yield % |
|---|---|---|---|---|
| 59 | NO₂—⌬—SO₂ | AcOEt 3 volumes | 123 | 92 |
| 36 | 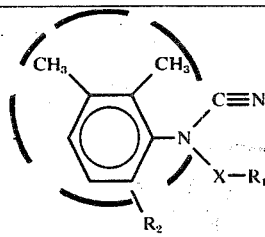 | nPrOH 15 volumes | 166–7 | 42 |
| 106 | Cl—⌬(CH₃)—O—CH₂—CO— | AcOEt 4.5 volumes | 153 | 33.5 |

TABLE-continued

| 107 | 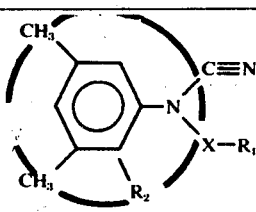 | Dichloroethane 10 volumes | 195 | 49.5 |
| --- | --- | --- | --- | --- |
| 108 | ClCH₂—CO | EtOH 4 volumes | 103 | 27.5 |

|  | Analysis | | | |
| --- | --- | --- | --- | --- |
|  | C % | H % | N % | Remarks |
| Calc. | 54.37 | 3.95 | | New |
| Found | 54.50 | 3.98 | | |
| Calc. | | | 8.02 | New |
| Found | | | 8.01 | |
| Calc. | | | 8.52 | New |
| Found | | | 8.43 | |
| Calc. | | | 7.30 | New |
| Found | | | 7.47 | |
| Calc. | | | 12.58 | New |
| Found | | | 12.31 | |

E) Formula:

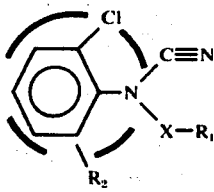

| Compound No. | X—R₁ | Recrystallisation | M.P. °C | Yield % |
| --- | --- | --- | --- | --- |
| 101 | EtO—CO— | EtOH 2 volumes | 63 | 88.5 |
| 104 | Cl—⌬—O—CH₂—CO— | EtOH 30 volumes | 146 | 72 |
| 102 | 2,4,5-Cl₃—C₆H₂—O—CH₂CO— | Dichloroethane 10 volumes | 193 | 59 |
| 105 | 3,4,5-(CH₃O)₃—C₆H₂—CO— | EtOH 7 volumes | 140 | 66.5 |

|  | Analysis | | | |
| --- | --- | --- | --- | --- |
|  | C % | H % | N % | Remarks |
| Calc. | | | 12.84 | New |
| Found | | | 12.88 | |
| Calc. | | | 8.87 | New |
| Found | | | 8.73 | |
| Calc. | | | 7.30 | New |
| Found | | | 7.25 | |
| Calc. | | | 8.21 | New |
| Found | | | 8.14 | |

F) Formula:

| Compound No. | X—R₁ | Recrystallisation | M.P. °C | Yield % |
| --- | --- | --- | --- | --- |
| 99 | EtO—CO | Liquid | $E_{0.15}=$ 134.7 | 86 |
| 87 | Cl—⌬—O—CH₂—CO | EtOH 20 volumes | 139 | 68 |

TABLE-continued

| 88 | Cl—⟨⟩—O—CH₂—CO | | EtOH 25 volumes | | | 156 | 41 |

| | | | | Analysis | | | |
|---|---|---|---|---|---|---|---|
| | | | | C % | H % | N % | Remarks |
| | | | Calc. | | | 12.47 | New |
| | | | Found | | | 12.47 | |
| | | | Calc. | | | 8.72 | New |
| | | | Found | | | 8.88 | |
| | | | Calc. | | | 7.87 | New |
| | | | Found | | | 7.53 | |

G) Formula:

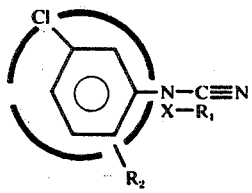

| Compound No. | X—R₁ | Recrystallisation | M.P. °C | Yield % |
|---|---|---|---|---|
| 111 | EtO—CO | $E_{0.3}=122°$ | 28–29.5 | 88.7 |
| 89 | Cl—⟨⟩—O—CH₂—CO— | EtOH 16 vol. | 132 | 58 |
| 90 | Cl—⟨⟩(Cl)—O—CH₂—CO | Dichloroethane 6 volumes | 150 | 29 |

| | | Analysis | | | |
|---|---|---|---|---|---|
| | | C % | H % | N % | Remarks |
| | Calc. | | | 12.47 | New |
| | Found | | | 12.57 | |
| | Calc. | | | 8.72 | New |
| | Found | | | 8.83 | |
| | Calc. | | | 7.87 | New |
| | Found | | | 7.65 | |

H) Formula:

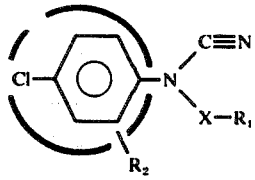

| Compound No. | X—R₁ | Recrystallisation | M.P. °C | Yield % |
|---|---|---|---|---|
| 91 | Cl—⟨⟩—O—CH₂—CO— | n-PrOH 9 volumes | 143 | 54 |
| 92 | Cl—⟨⟩(Cl)—O—CH₂—CO— | Dichloroethane 10 volumes | 183 | 53 |

| | | Analysis | | | |
|---|---|---|---|---|---|
| | | C % | H % | N % | Remarks |
| | Calc. | | | 8.72 | New |
| | Found | | | 8.63 | |
| | Calc. | | | 7.87 | New |
| | Found | | | 7.75 | |

I)

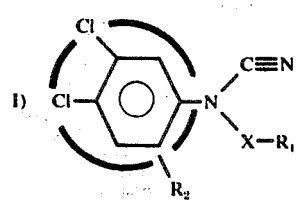

| Compound No. | X—R₁ | Recrystallisation | M.P. °C | Yield % |
|---|---|---|---|---|
| 94 | EtO—CO— | Hexane 10 volumes | 55 | 70 |

TABLE-continued

| | | | | | |
|---|---|---|---|---|---|
| 83 | Cl-C6H4-O-CH2-CO- | | AcOEt 12 volumes | 175 | 51 |
| 84 | (2-Cl, 4-Cl)-C6H3-O-CH2-CO- | | Dichloroethane 20 volumes | 195 | 45 |

| | Analysis | | | |
|---|---|---|---|---|
| | C % | H % | N % | Remarks |
| Calc. | | 10.81 | | New |
| Found | | 10.62 | | |
| Calc. | | 7.87 | | New |
| Found | | 7.84 | | |
| Calc. | | 7.18 | | New |
| Found | | 7.00 | | |

J) Formula:

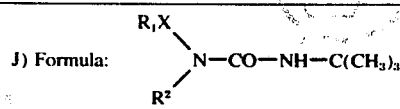

$N-CO-NH-C(CH_3)_3$ with $R^1X$ and $R^2$

| Compound No. | $R^1X$ | $R^2$ | Recrystallization | M.P. °C | Yield % |
|---|---|---|---|---|---|
| 40 | CH3-C6H4- | C6H5-CO | EtOH 7 volumes | 125 | 27.5 |
| 31 | H | (CH3O)3-C6H2-CO- | Iso ether 76 volumes | 120 | 60 |
| 53 | CH3O-C6H4- | (2-NO2)-C6H4-SO2 | EtOH 4 vol. | 30 | 83.5 |
| 56 | C6H5- | (2-NO2)-C6H4-SO2 | EtOH 4 vol. | 155 | 68.4 |

| | m Analysis | | | |
|---|---|---|---|---|
| | C % | H % | N % | Remarks |
| Calc. | 73.52 | 7.14 | | New |
| Found | 73.64 | 7.07 | | |
| Calc. | 58.05 | 7.14 | 9.02 | New |
| Found | 57.95 | 7.09 | 9.08 | |
| Calc. | 52.23 | 5.41 | 10.92 | New |
| Found | 55.03 | 5.37 | 10.77 | |
| Calc. | 54.10 | 3.08 | 11.13 | New |
| Found | | | | |

K) Formula:

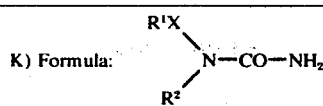

$N-CO-NH_2$ with $R^1X$ and $R^2$

| Compound No. | $R^1X$ | $R^2$ | Recrystallisation | M.P. °C | Yield % |
|---|---|---|---|---|---|
| 97 | CH3-C6H4- | EtOCO- | EtOH 8 vol. | 196-8 | 75.5 |
| 100 | (2-Cl)-C6H4- | EtO-CO | EtOH | 152 | 86 |
| 96 | (3-Cl)-C6H4- | EtO-CO- | EtOH 15 vol. | 177 | 55 |

| | Analysis | | | |
|---|---|---|---|---|
| | C % | H % | N % | Remarks |
| Calc. | | | 12.61 | New |
| Found | | | 12.58 | |

TABLE-continued

| | | | |
|---|---|---|---|
| | Calc. | 11.55 | New |
| | Found | 11.69 | |
| | Calc. | 11.46 | New |
| | Found | 11.54 | |

It is obvious that the foregoing Examples of the present invention have been described solely by way of explanation and without limitation, and that any useful modification could be made to it without departing from its scope as defined in the following claims.

We claim:

1. A process for producing compounds of the general formula:

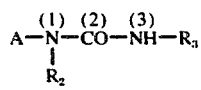

in which A is hydrogen or a monovalent group $R_1 - X$ (in which X is $-CO$ or $-SO_2$, and $R_1$ is alkyl, cycloalkyl, aralkyl, alkoxy, aryl, aryloxy, or etheroxy), $R_2$ is hydrogen, alkyl, cyclo-alkyl, aralkyl, or aryl, and $R_3$ is hydrogen or an alkyl radical derived from a secondary or tertiary alcohol, with the restriction that, when $R_2$ is hydrogen, $R_3$ is alkyl and that when $R_3$ is hydrogen, $R_2$ is alkyl, cycloalkyl, aralkyl, or aryl, said process comprising reacting a cyanamide of the formula:

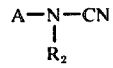

(in which A and $R_2$ have the meanings given above), with a compound adapted to readily form a carbo cation ($R_3^+$) selected from the group consisting of tertiary alcohols, secondary alcohols and unsaturated compounds, in the presence of a catalyst of sulfuric acid or a Lewis acid.

2. A process according to claim 1, in which the catalyst is sulphuric acid.

3. A process according to claim 1, in which the catalyst is boron fluoroetherate and the reaction is effected in the presence of a solvent for the starting cyanamide.

4. A process according to claim 1 wherein $R_3$ is tertiary butyl, and said compound adapted to readily form a carbo cation is tertiary butyl alcohol.

5. A process according to claim 1 wherein $R_3$ is an alkyl derived from a tertiary alcohol, and said compound adapted to readily form a carbo cation is selected from the group consisting of tertiary alcohols.

* * * * *